(12) United States Patent
Guillet

(10) Patent No.: US 7,594,949 B2
(45) Date of Patent: *Sep. 29, 2009

(54) CROSS-LINKED POLYMERIC NANOPARTICLES AND METAL NANOPARTICLES DERIVED THEREFROM

(75) Inventor: James E. Guillet, Don Mills (CA)

(73) Assignee: G-Nano, LLC, Roanoke, VA (US)

(*) Notice: Subject to any disclaimer, the term of this patent is extended or adjusted under 35 U.S.C. 154(b) by 491 days.

This patent is subject to a terminal disclaimer.

(21) Appl. No.: 11/412,964

(22) Filed: Apr. 28, 2006

(65) Prior Publication Data

US 2006/0191373 A1  Aug. 31, 2006

Related U.S. Application Data

(63) Continuation of application No. 10/275,978, filed as application No. PCT/CA01/00757 on May 28, 2001, now Pat. No. 7,189,279.

(30) Foreign Application Priority Data

May 26, 2000 (CA) .................................. 2309575

(51) Int. Cl.
B22F 9/24 (2006.01)
B22F 1/02 (2006.01)

(52) U.S. Cl. ....................... 75/362; 75/252; 977/776; 977/777

(58) Field of Classification Search .................. 75/776, 75/777, 362, 369; 977/776, 777
See application file for complete search history.

(56) References Cited

U.S. PATENT DOCUMENTS

| 3,515,539 A | 6/1970 | Wethem |
| 4,107,288 A | 8/1978 | Oppenheim et al. |
| 4,329,332 A | 5/1982 | Couvreur et al. |
| 4,753,986 A | 6/1988 | Wang |
| 5,041,516 A | 8/1991 | Frechet et al. |
| 5,118,528 A | 6/1992 | Fessi et al. |
| 5,141,814 A | 8/1992 | Anderson et al. |
| 5,215,820 A * | 6/1993 | Hosokawa et al. .......... 428/403 |
| 5,244,737 A | 9/1993 | Anderson et al. |
| 5,562,099 A | 10/1996 | Cohen et al. |
| 5,629,353 A | 5/1997 | Steckle, Jr. et al. |
| 5,641,515 A | 6/1997 | Ramtoola |
| 5,686,518 A | 11/1997 | Fontenot et al. |
| 5,705,196 A | 1/1998 | Galan Valdivia et al. |
| 5,756,573 A | 5/1998 | Trumbo et al. |
| 5,766,635 A | 6/1998 | Spenleuhauer et al. |
| 5,766,764 A * | 6/1998 | Olli et al. ..................... 428/407 |
| 5,874,111 A | 2/1999 | Maitra et al. |
| 5,891,357 A | 4/1999 | Akashi et al. |
| 5,972,356 A | 10/1999 | Peffley et al. |
| 5,998,523 A * | 12/1999 | Grunbauer et al. .......... 524/403 |
| 6,090,858 A | 7/2000 | El-Sayed |
| 6,117,454 A | 9/2000 | Kreuter et al. |
| 6,146,663 A | 11/2000 | Bissery et al. |
| 6,254,890 B1 | 7/2001 | Hirosue et al. |
| 6,268,222 B1 | 7/2001 | Chandler et al. |
| 6,479,146 B1 | 11/2002 | Caruso et al. |
| 6,890,703 B2 | 5/2005 | Hawker |
| 7,189,279 B2 | 3/2007 | Guillet |
| 2003/0177868 A1 | 9/2003 | Guillet |
| 2006/0191374 A1 | 8/2006 | Guillet |

FOREIGN PATENT DOCUMENTS

| DE | 19918627 A1 | 10/2000 |
| EP | 0268498 A2 | 5/1988 |
| EP | 0303803 A2 | 2/1989 |
| EP | 0336779 A2 | 10/1989 |
| EP | 0520889 A1 | 12/1992 |
| EP | 0877033 A1 | 11/1998 |
| GB | 2288601 A | 10/1995 |
| JP | 10330406 | 12/1998 |

* cited by examiner

Primary Examiner—Roy King
Assistant Examiner—Ngoclan T Mai
(74) Attorney, Agent, or Firm—Townsend and Townsend and Crew, LLP

(57) ABSTRACT

There are provided internally cross-linked, stables polymeric materials, in the form of substantially spherical particles, each particle consisting essentially of a single macromolecule. They have the unusual property of being soluble or dispersible in a liquid medium without significantly increasing the viscosity of the medium, rendering them potentially useful in imaging applications such as ink jet printers. They can be prepared by dissolving polymeric material in a solvent system to form a solution of the polymeric material at a concentration therein of less than the critical concentration for the polymer, causing the polymeric material to contract into an approximately spheroidal conformation in solution, cross-linking the polymeric material in solution in said spheroidal conformation so assumed, and recovering stable, cross-linked approximately spheroidal polymeric particles from the solution.

17 Claims, 5 Drawing Sheets

US 7,594,949 B2

CROSS-LINKED POLYMERIC NANOPARTICLES AND METAL NANOPARTICLES DERIVED THEREFROM

RELATED APPLICATIONS

This application is a continuation of application Ser. No. 10/275,978, filed on May 23, 2003 now U.S. Pat. No. 7,189, 279, which is incorporated herein in its entirety by reference thereto, which claims priority to PCT/CA01/00757 filed on May 28, 2001 (which is incorporated by reference herein in its entirety), which claims priority to Canadian patent application 2,309,575 filed on May 26, 2000 (which is incorporated by reference herein in its entirety).

FIELD OF THE INVENTION

This invention relates to polymers, and methods for producing polymers of novel structure. More particularly, it relates to a process for cross-linking polymers to produce cross-linked polymers stabilized into particularly useful, dense structures. It also relates to novel polymeric materials having unusual properties.

BACKGROUND OF THE INVENTION

It is known that cross-linking of polymers substantially alters the physical properties of the polymers. Cross-linking can change a thermoplastic polymer to a thermoset polymer, can alter its solubility, density and other physical characteristics. Normally, cross-linking of a polymer is an irreversible process, so that the shape, configuration and density of a cross-linked polymer remain substantially permanent once the cross-linking process is complete.

A variety of different methods of polymer cross-linking are known. One method is reaction with chemical cross-linking reagents. This is particularly applicable where the starting polymer is unsaturated (polybutadiene, polyisoprene, styrene-butadiene copolymers, EPDM etc.), so that the groups of unsaturation take part in the cross-linking. Other methods involve creation of reactive sites such as free radicals on the polymer chains, e.g. by hydrogen abstraction using a free radical-generating initiator, by irradiation with γ-rays, X-rays, etc. Cross-linking can take place with the polymer in solution in a suitable solvent, in suspension or in bulk. Cross-linking is normally a random process, which may involve links between different polymer chains and links between points on the same polymer chain, and permits only limited control over its course and extent. In solution and suspension, non-cross-linked polymers tend to adopt an extended, coiled conformation, which is altered in a generally uncontrollable manner during cross-linking. There is a need for stable, solid particulate polymers of predetermined shape, size and density, for use for example in ink-jet printers, photocopiers and other imaging applications, where the achievement of fine definition and resolution of images depends upon the particle size and uniformity of the particles comprising the imaging medium, and on the viscosity of the imaging medium.

SUMMARY OF THE INVENTION

The present invention provides a process whereby polymers in solution are diluted so as effectively to disentangle and isolate the individual macromolecules from one another in the solution, and then caused to contract from the normal, random coil conformation to adopt an approximately spheroidal configuration. Then the macromolecules are stabilized in this conformation, e.g. by applying cross-linking conditions to the solution, so that the dissolved polymer is internally stabilized in its newly assumed, spheroidal configuration, to form independent particles stabilized in that conformation. In essence, the particles are single macromolecules, independent of other, surrounding macromolecules.

By means of the present invention, dense, spherical particles of polymers can be made, having a high degree of uniformity as to particle size, shape and density. The particle size is largely a function of molecular weight of the polymer, a parameter which is controllable by known methods, during polymerization. Polymers of very narrow molecular weight distribution can be made by known methods of polymerization, and these will lead to stabilized polymer particles of substantially uniform particle size, following the method of the present invention. A solution of the polymer is first prepared using a solvent or mixture of solvents in which the polymer fully dissolves, and at a concentration below the critical concentration, and caused to contract into a spheroidal conformation. Then the polymer is stabilized, e.g. by cross-linking. Polymer particles of very small size, average diameter in the range 0.1-10 nanometers (nanoparticles), can be made in this way.

The resulting polymeric materials are internally cross-linked macromolecules, i.e. substantially all of the cross-links are between groups on the same polymer chain as opposed to cross-links between groups on different polymer chains to bond the polymer chains together in a network. These internally cross-linked polymers according to the invention have solution properties which are quite different from those of the same polymeric material either before cross-linking or after cross-linking in bulk. Conventional high molecular weight polymers (100,000 and higher) have high viscosity in solution, resulting at least in part from entanglement of and interaction between individual macromolecules. If such a polymer is cross-linked in the bulk phase, the resulting polymer will not dissolve in any solvent, but may swell when contacted with solvents. Internally cross-linked materials of the invention, in contrast, even with molecular weights in excess of 1,000,000 can be dispersed in a wide variety of solvents and non-solvents, but scarcely affect the viscosity of the solution or dispersion at all. This remarkable property makes these new compositions of the invention of potential utility not only in imaging compositions as described above, but also in drug delivery applications.

Thus according to one aspect of the present invention, there is provided a process for preparing polymeric material in the form of stable nanoparticles having substantially spherical particulate form, which comprises:

dissolving a polymeric material in a solvent system to form a solution of the polymeric material at a concentration therein of less than the critical concentration for the polymeric material;

causing the macromolecules of said polymeric material to contract into an approximately spheroidal conformation in solution;

and stabilizing the polymeric material in solution in said spheroidal conformation so assumed by creating intra-molecular bonds.

Stable, intra-molecularly bonded, approximately spheroidal polymeric nanoparticles can be recovered from the solution, if desired, by standard methods.

The term "intra-molecularly bonded" as used herein indicates the presence of internal cross-links or other bonds linking parts of the same macromolecule to itself, to the substantial exclusion of bonds linking different macromolecules together ("inter-molecular bonds").

According to another aspect, the invention provides internally cross-linked particulate independent macromolecules having substantially spheroidal particle shapes, said particles having the ability to be dispersed in a liquid medium without significantly changing the viscosity of the medium.

BRIEF REFERENCE TO THE DRAWINGS

FIG. 1 of the accompanying drawings is a digrammatic illustration of a preferred process according to the invention;

DESCRIPTION OF THE PREFERRED EMBODIMENTS

Figure 1:
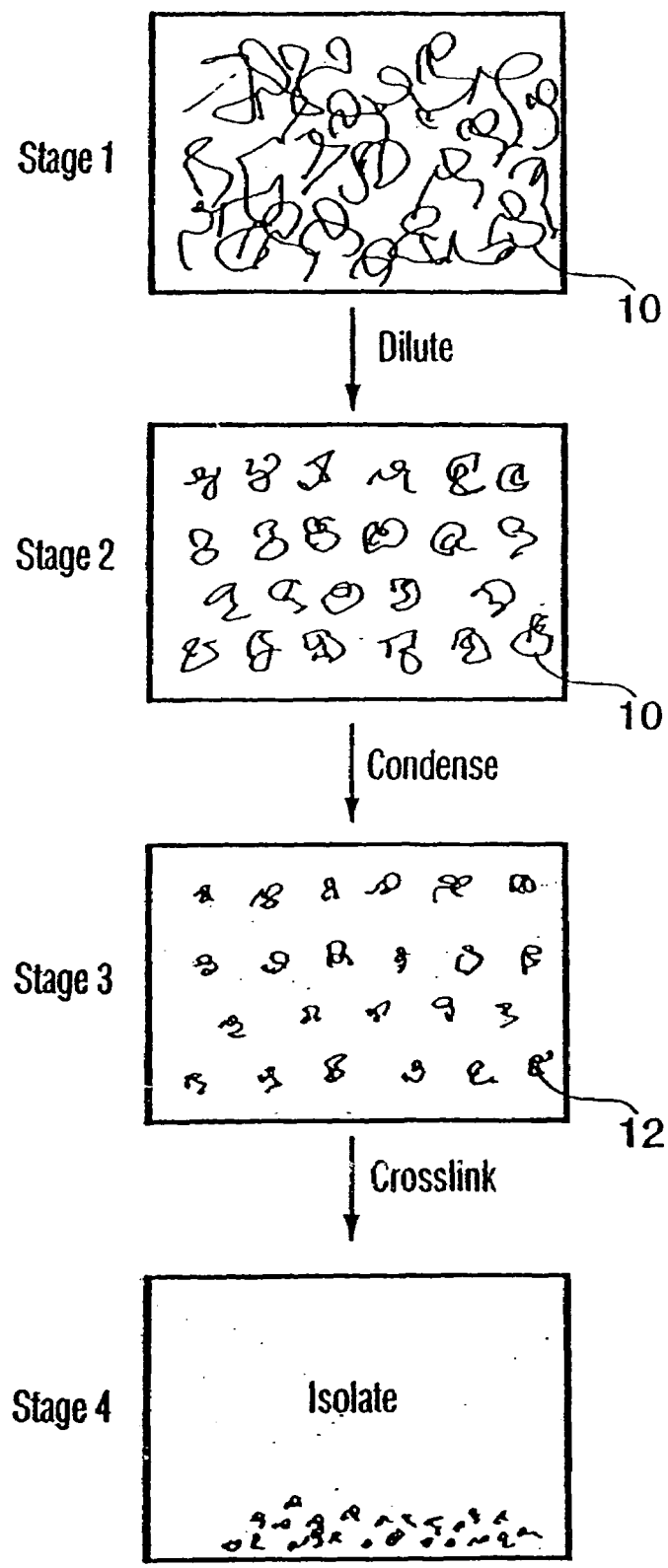

The process of the present invention is applicable to a wide variety of polymeric materials, natural and synthetic. The polymeric materials can be homopolymers or copolymers of two or more monomers, including block copolymers and graft copolymers. It is necessary that the chosen polymeric material be soluble to a substantial extent in at least one solvent system, so as to enable it to adopt a contracted spheroidal conformation in solution, as described below.

The chosen polymeric material is first dissolved in an appropriate solvent system. This may be water, an organic solvent or a mixture of two or more such solvents. The polymeric material is dissolved such that, in solution individual macromolecules thereof remain distinct, separated and non-entangled with one another. This can be achieved by arranging that the concentration of polymer in solution is below the "critical concentration," which is the concentration at which the individual polymer chains in the solution interpenetrate. The separated, non-interpenetrating macromolecules in solution can be condensed e.g. by changing the solution characteristics, and stabilized by internal cross-linking, to a particle size which, assuming spherical shape, can be calculated from the molecular weight of the polymer. The ability of the macromolecules to achieve a condensed particle size largely in accordance with theoretical calculations, assuming spheroidal shape, acts as a check or test that the polymer in solution, prior to condensation and cross-linking, was indeed in the form of independent, separated, non-interpenetrated macromolecules for the initial stages of the process of the present invention. A person skilled in the art can readily conduct such calculations from a knowledge of the chemistry and molecular weight of the polymer under consideration, and simple experiments to determine particle size after stabilization as described. Comparison of this with theoretical calculation and prediction can determine the critical concentration for the specific polymer solution.

Either as it dissolves (for example in the case of sodium styrene sulfonate-vinyl naphthalene copolymers and similar copolymers), or by reduction of the solvent power of the solution, for example by adding to it a precipitating non-solvent, or a salt which changes the ionization conditions of the solution, the polymer is caused to condense and to contract to dense spheroidal structures. Then it is internally stabilized preferably by cross inking, using a system which is compatible with the chosen polymer and the chosen solvent system, for example by exposure to γ-radiation. When each polymer molecule contains three or more internal cross-links, it can no longer expand to form its normal random coil configuration in solution. Instead, it retains its spheroidal confirmation, the density of which increases with the degree of cross-linking. In the case of some polymers, e.g. those having mutually reactive chemical groups such as polypeptides, stabilization may occur by reaction of these groups with one another as the polymer is caused to condense and contract, e.g. by formation of disulphide bridges, without application of a specific cross-linking step.

A wide variety of polymers and copolymers can be used in the present invention, provided only that a suitable solvent system is available for them, and that the random coils can be condensed to denser spheroidal particles prior to cross-linking. Preferred polymers have ionic charges (polyelectrolytes) so that, in the preferred aqueous solvent systems, the macromolecules are mutually repellant and less likely to agglomerate prior to cross-linking.

Examples of useful polymers in the present invention include polymers and copolymers derived from such monomers as styrene, vinyl naphthalene, styrene sulphonate, vinylnaphthalene sulphonate, acrylic acid, methacrylic acid, methylacrylate, acrylamide, methacrylamide, acrylates, methacrylates, acrylonitrile, N-loweralkyl acrylamides and the like.

One preferred embodiment of the invention involves the use of polymers having a critical solution temperature, i.e. a temperature below which they are soluble in water, and above which they are insoluble in water. Using the process of the present invention, such polymers can be dissolved in water, caused to assume a condensed, spheroidal conformation and internally cross-linked as described. They can then be used for delivery and controlled release of other organic compounds such as drugs. The drug can be dispersed in a suspension of the cross-linked polymer at a temperature above the critical solution temperature, at which the drug will be absorbed by the polymer in its collapsed-particulate form. When the temperature is reduced below the critical solution temperature, the polymer particle swells and slowly releases the drug. Polymers having critical solution temperatures include polymers of N-isopropylacrylamide (NIPAM), the critical solution temperature of which can be adjusted by copolymerization with other monomers.

FIG. 1 of the accompanying drawings diagrammatically illustrates a process according to an embodiment of the invention. At stage 1, the polymer exists in a concentrated solution, in which the macromolecule chains 10 are intertwined and interpenetrated, so that any attempt to cross-link them at this stage would cause inter-reaction between the polymer chains.

Upon dilution of the solution, stage 2, below the critical concentration, the polymer macromolecules 10 are spaced apart from one another, but still in their random coil configuration. Upon reducing the solvent power of the solvent system, e.g. by introducing a non-solvent or a salt, the macromolecules condense, stage 3, into generally spherical conformation 12, and can now be cross-linked, eg. by application of ionizing radiation, at stage 4, whereupon internal cross-linking, as opposed to inter-macromolecular cross-linking occurs, effectively locking the macromolecules into the configurations assumed in stage 3. Then the cross-linked, approximately spherical macromolecule particles can be recovered e.g. by freeze drying, for use in applications referred to above.

When the macromolecule particles are re-dissolved e.g. in water, they have very little, if any, effect on the viscosity of the solvent (in any event less than a 10% resulting increase in the viscosity). This is due to the fact that the macromolecules do not agglomerate to any significant extent, nor do they expand or mutually interact to any significant extent. This unusual property renders the nanoparticles useful in a number of specialty applications. The nanoparticle macromolecules having critical solution temperature as described above are, for example, especially useful as drug carriers, where drugs are associated with the polymers in solution and delivered to very small veins and capillaries of the body, e.g. certain areas of the brain, which are so small that they cannot be penetrated by drug solutions of other than very low viscosity.

Whilst water is the preferred solvent for use in the present invention, other polar solvents can also be used if desired, alone or in mixtures with each other and in admixture with water. The best choice of solvent depends to a large extent on the choice of polymer. Polar solvents such as lower alkanols, ketones, amines, dimethylsulfoxide and the like are suitable alternatives to water, when working with a polymer of limited solubility in water.

Another aspect of the present invention comprises the use of internally cross-linked macromolecules as described above in the preparation of nanoparticles of metals, i.e. metal particles which are substantially spherical in shape, and which have an average diameter in the range 0.1-10 nanometers, preferably from 0.1-8 nanometers and more preferably from 0.1-5 nanometers. Such nanoparticles of metals comprise another aspect of the invention. This process aspect uses internally cross-linked polymers as described above, in which the polymer is a polyelectrolye such as polyacrylic acid or a salt thereof e.g. sodium polyacrylate. For example, by dissolving them in water containing a large excess of ferrous ions, the sodium ions can be replaced by ferrous ions. After removal of the sodium ions, the particles can be heated in air or oxygen to above 200-300° C. The polymer content is largely removed by pyrolysis, leaving extremely small particles of iron oxide with very large surface area and important electrical and catalytic properties. If the process is carried out in a reducing atmosphere, high surface metal particles can be obtained. Other metal salts such as silver salts (silver nitrate for example), copper salts and gold salts can be used to produce finely divided metal particles useful in imaging and, because of their very high surface area, in catalysis. Palladium, platinum, titanium and molybdenum are examples of metals which can be prepared in nanoparticle form according to the present invention, for use in catalysis. Substantially any metal which is stable in its metallic form and which has a water soluble salt can be used in this way. The metal salt can be dialyzed against the sodium polyacrylate (or similar polymeric salt) particles of the invention, to remove the alkali metal and replace it with the other metal. Then the product is reduced, e.g. by application of laser radiation, and solid metal nanoparticles e.g. silver particles, in some cases surrounded by a fine layer of residual polymer which has a stabilizing effect, are obtained.

In another modification, ionic groups on internally cross-linked polymers of the present invention, for example the sodium acrylate groups in the particles made in examples 1, 2 and 8 below, can easily be converted to other useful functional groups. Sodium acrylate groups for example can be converted converted to the corresponding acid chloride by treatment with thionyl chloride. Dye molecules containing reactive hydroxyl or amino groups can then be permanently bound to both the surface and the interior of the particles giving rise to products useful in imaging applications such as in ink-jet printing.

The invention is further described with reference to the following specific illustrative examples.

EXAMPLE 1

Internally Cross-linked Polyacrylic Acid

Figure 2:
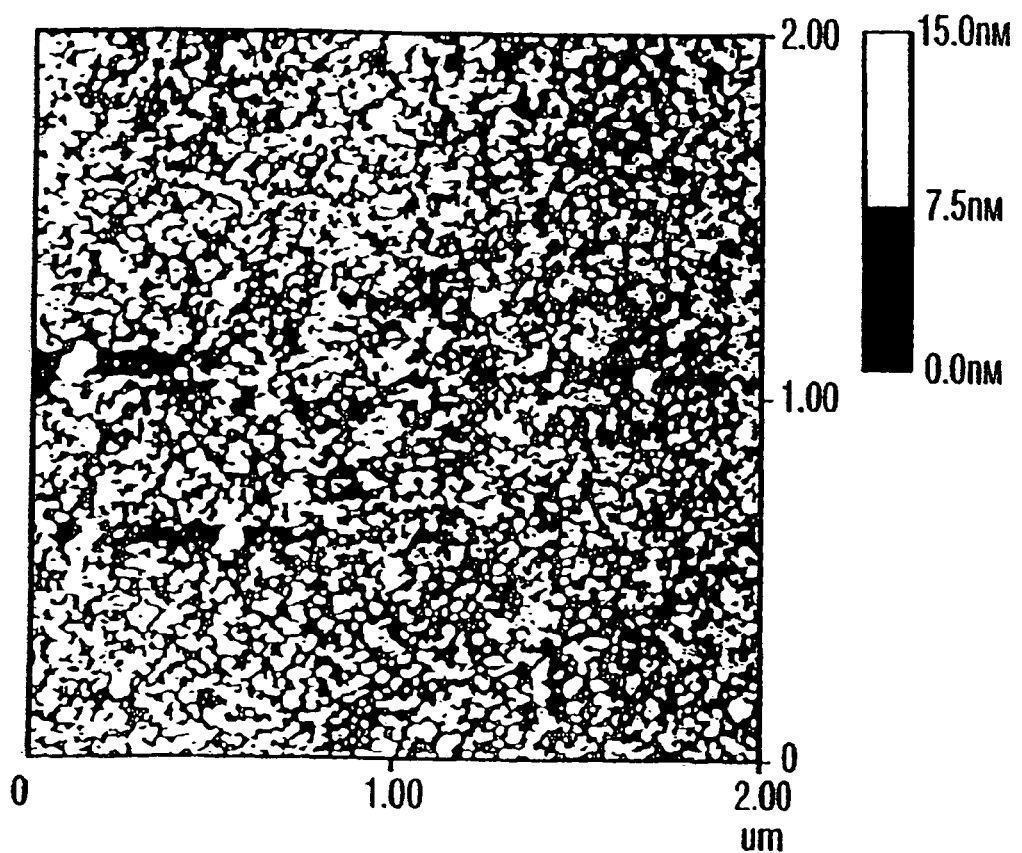
FIG. 2 is an atomic force microscopy picture of one product of Example 1 below.

The sodium salt of poly(acrylic) acid (Polysciences Inc. Cat#18755), of molecular weight of 1,300,000, was used in a cross-linking process according to the invention. 97 mg of polymer was dissolved in 100 ml of distilled water. After solution was complete the pH was 8.2, and 98 mg of sodium chloride was slowly added to cause the polymer particles to contract. 5 cc. of the solution was flushed with nitrogen, sealed in a glass vial, and irradiated with 10 megarad of $Co^{60}$ γ radiation. After radiation the vial was opened and the solution dialysed against water for 5 days to remove the salt, and the polymer particles recovered by freeze drying under vacuum. The particles were studied by atomic force microscopy (A.F.M) (film cast onto mica, to produce tapping mode AFM height image) and shown to be perfectly spherical, with diameters of 6 to 10 nanometers (see FIG. 2). No such particles were observed in the uncross-linked control sample. The particles observed are close to the size calculated for a completely collapsed macromolecular chain of molecular weight one million. When dispersed in water at a concentration of 1%, the solution had a viscosity virtually the same as pure water. At the same concentration a water solution of uncross-linked starting material was much more viscous.

Figure 3:
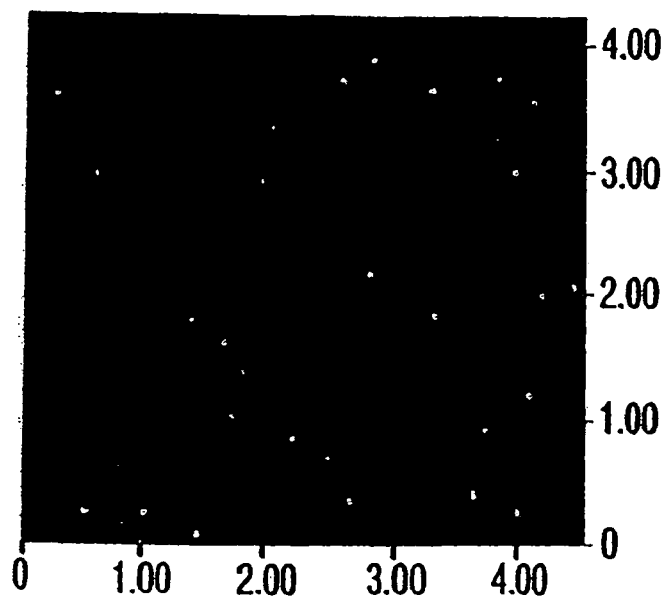
FIG. 3 is an atomic force microscopy picture of another product of Example 1 below.

The procedure was repeated with a polyacrylic acid (sodium salt) of molecular weight about 700,000, and the A.F.M. picture of this product is presented as FIG. 3 hereto. The spherical shape of the particles is clearly apparent from this picture. The scale on the Figure is in millimicrons. The particles have a diameter of approximately 4 nanometers (0.4 millimicrons).

EXAMPLE 2

The procedure of Example 1 was repeated except that before addition of the sodium chloride the pH of the solution was reduced to 3.2 by addition of small amounts of 0.1 N hydrochloric acid. After addition of sodium chloride and cross-linking with 10 megarad of γ-rays, nanoparticles of the same size (6-10 nanometers) were observed as in Example 1 by A.F.M.

EXAMPLE 3

Copolymers of sodium styrene sulfonate and vinyl naphthalene containing about equal quantities of each comonomer are known to form hypercoiled pseudomicellar conformations in water, i.e. they do not form expanded random coils, but are collapsed into much smaller spherical structures with much higher coil density due to the hydrophobic interactions between the naphthalene groups and water. These particles are negatively charged due to the ionization of the styrene sulfonate groups in water. The polymers can also be internally cross-linked by the following procedure. A polymer containing 50% by weight sodium styrene sulfonate and 50% of vinyl naphthalene was prepared in benzene solution AIBN as catalyst. After isolation and purification by dialysis against pure water it had a molecular weight $M_w$ of 200,000.

Figure 4:
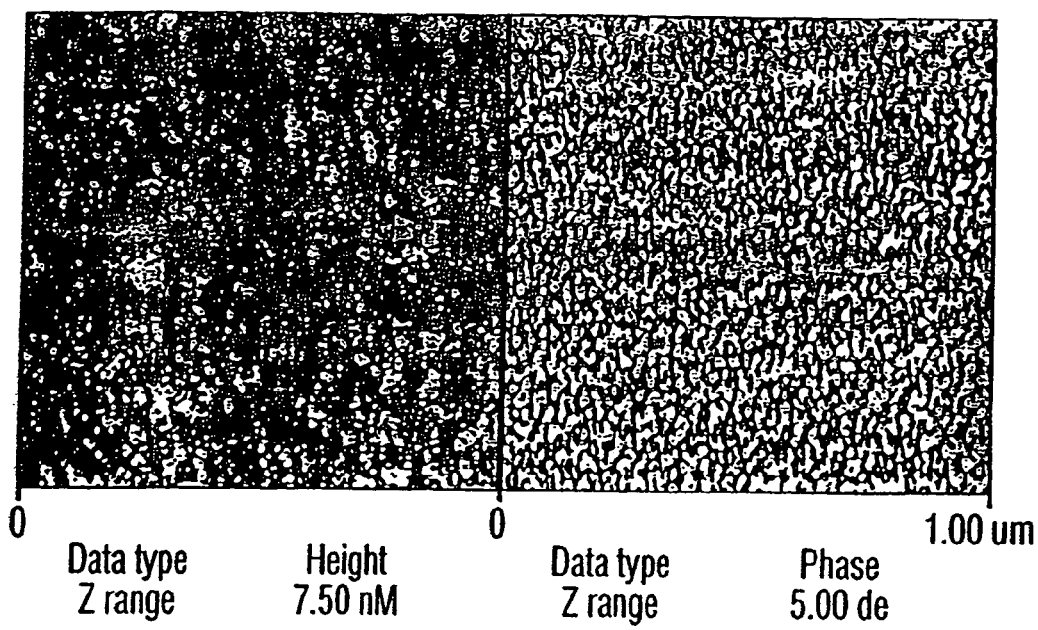
FIG. 4 is an atomic force microscopy picture of the product of Example 3 below.

100 mg of this polymer was dissolved in 100 ml distilled water and after purging with oxygen-free nitrogen was irradiated with a dose of 0.40 megarad of Cobalt$^{60}$ γ-rays. A.F.M. analysis of the resulting particles showed spherical particles with an average diameter of 7.5 nanometers. The A.F.M. picture of the particles is presented as FIG. 4 hereof. A 1% solution of these particles in water showed very little increase over that of water itself.

EXAMPLE 4

Internal cross-linking can be carried out by other means besides γ radiation. In some cases, irradiation of the aqueous dispersion with high intensity U.V. laser light will cause internal cross-linking. A simpler procedure is to prepare a copolymer with a small number of double bonds which can be connected by vinyl polymerization. In this example a copolymer of 50% styrene sulfonate and 48% vinyl naphthalene and 2% divinyl benzene was prepared as in Example 3. 100 mg of this polymer was dissolved in 100 ml of water to which was slowly added with stirring 1.0 cc of benzene containing 4 mg styrene and 1 mg of AIBN (azobis-iso-butyryl nitrile). After purging with nitrogen 2 cc of this mixture was heated to 70° C. for 5 hours with stirring. After isolation and purification by dialysis spherical nanoparticles were observed by A.F.M.

EXAMPLE 5

An additional 2 cc of the solution prepared in Example 4 was shaken with a small amount of styrene monomer and allowed to separate. Excess styrene was removed and the polymer was internally cross-linked by exposure of the solution to near ultraviolet light (λ=313 nm from the American Ultraviolet Irradiation System for 1 hour. After isolation and purification cross-linked nanoparticles with the viscosity properties of the γ irradiated materials from Example 1 and 2 were produced.

EXAMPLE 6

Poly N-isopropyl acrylamide (NIPAM) is an important polymer which is often used in drug delivery systems. It has a lower critical solution temperature (LCST) of 31° C. It is soluble in water below this temperature but precipitates sharply above this. This temperature can be lowered by copolymerization with hydrophobic monomers such as acrylonitrile and raised by hydrophilic monomers such as acrylamide. These co-polymers can be internally cross-linked by any of the procedures described above. In a specific example 100 mg of polyNIPAM with a molecular weight of 200,000 g/mole was dissolved in 100 ml water at 20° C. and was cross-linked with 10 megarads of γ radiation. After isolation and purification, the internally cross-linked 5-10 nm nanoparticles can be used for the controlled delivery of other organic compounds. For example the drug can be absorbed by the collapsed particle in a water dispersion above LCST. After removal of the unabsorbed drug, the dispersion will remain stable until the temperature of the water is reduced below LCST, at which point the particle swells and slowly releases the drug. Since the size of the internally cross-linked nanoparticle is extremely small (~10 nm) it can access almost any part of the human body including the smallest blood capillaries which makes it of interest in a variety of medical therapies. The delivery polymers can also be made sensitive to pH instead of temperature.

EXAMPLE 7

Polymers such as NIPAM, polyacrylamide and polyethylene oxide, which do not contain ionized groups, are difficult to keep separate in water solution while the cross-linking process is taking place. This reduces the yield and purify of the desired internally cross-linked nanoparticles. Cleaner products and higher conversions can be achieved by including an ionizable comonomer. A copolymer of 2% acrylic acid and 98% NIPAM was prepared. At a pH of about 8-9 in water most of the acrylic acid units will be ionized, thus giving a strong negative charge to each polymer molecule. At high dilution, this prevents the agglomeration of individual chains to form larger particles. 100 mg of this polymer was internally cross-linked by the procedure of Example 6. A.F.M. studies of the internally cross-linked particles showed a much lower concentration of larger agglomerated particles than those prepared in Example 6.

EXAMPLE 8

A solution of sodium polyacrylate was prepared as in Example 1, and after the addition of sodium chloride, 4 mg of 4,4'-diazidostilbene-2,2' sodium sulfite dissolved in 1 cc benzene was added slowly with continuous stirring. After flushing with nitrogen, the ampoule was sealed and irradiated for 1 hour with 313 nm U.V. light in the American Ultraviolet Irradiation system. After irradiation the product was isolated by freeze drying and purified by dialysis as in Example 1. A.F.M. measurements showed particles similar to those found in Example 1.

EXAMPLE 9

Nanoparticles of Metal

Figure 5:
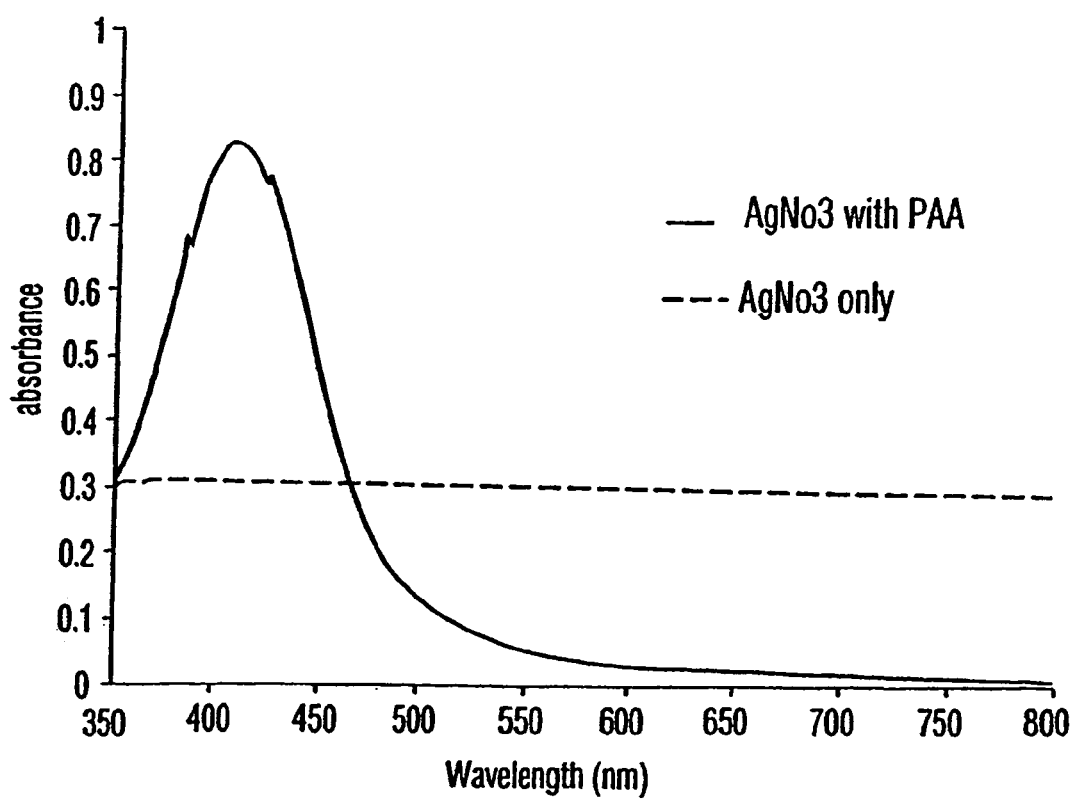
FIG. 5 is the UV-visible spectrum of the product of Example 9 below.

Nanoparticles of polyacrylic acid sodium salt prepared according to Example 1 were dialysed against dilute hydrochloric acid to remove the sodium ions, and then treated with excess silver nitrate in aqueous solution to form the silver salt of the acrylic acid groups in the polymer particles. Irradiation of these particles in aqueous dispersion with γ-radiation (10 Mrad) gave a dark orange solution. The UV-visible spectrum shown in FIG. 5 shows peaks corresponding to the well-known surface plasmon of silver colloids of size smaller than the wavelength of light, indicating that the silver ions have been reduced to metallic silver. The silver colloids are much more stable than those reported in the literature, as indicated by the fact that the plasmon band intensity did not change for many weeks after preparation.

Figure 6:
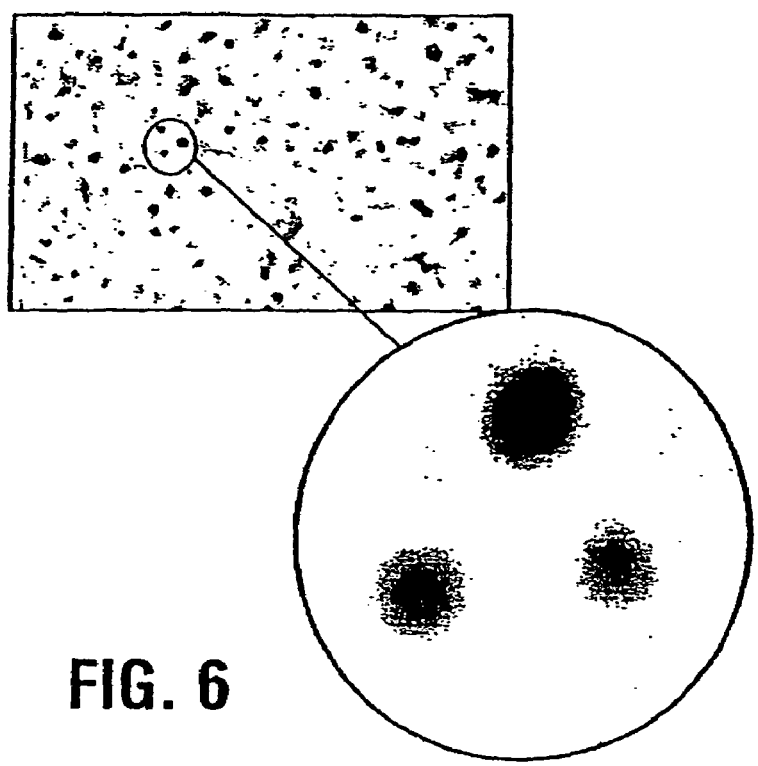
FIG. 6 is an electron microscope image, with an enlargement of the circled portion, of the product of Example 9 below.

After isolation of the particles and drying of them, spherical particles of diameter about 5 nm were observed by AFM. An electron microscope examination (TEM), FIG. 6, shows that the spherical silver particles are surrounded by a hazy region believed to be unreacted polymer, a possible factor in the enhanced stability of the silver nanoparticles.

Figure 7:
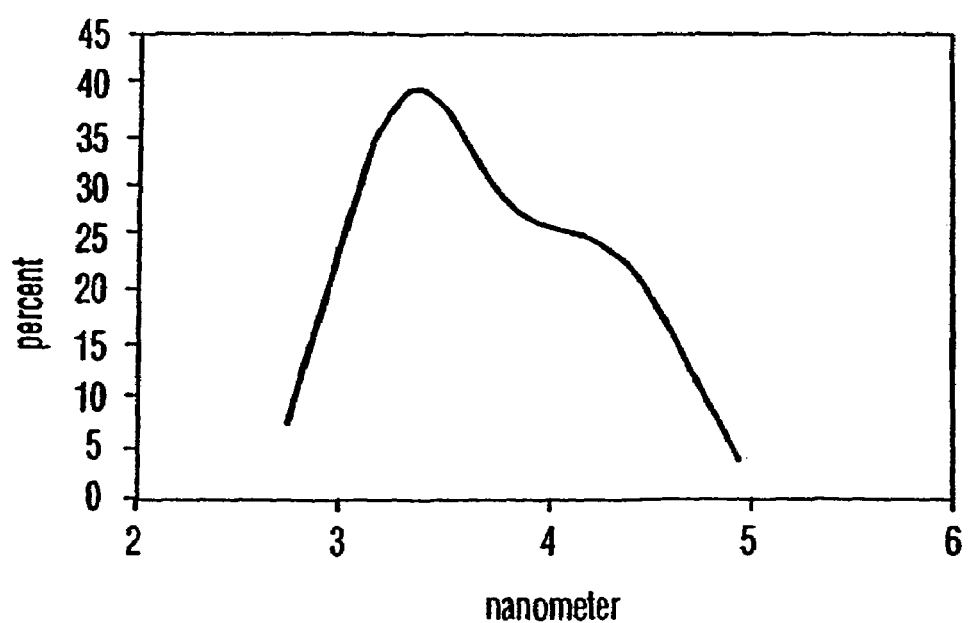
FIG. 7 is a curve showing the size distribution of the metal particles of Example 9 below.

The average diameter of the reduced silver particles was 3.5±0.53 nm. The diameter of the exterior, including the hazy region, was 5.2±0.8 nm. The particle size distribution is shown on FIG. 7.

Similar results were obtained by irradiation of the original salt particles with an intense laser pulse from a picosecond quadrupled Nd:YAG laser or XeF excimer laser, and by a chemical reducing agent such as sodium in liquid ammonia.

Similar experiments with iron and copper salts gave similar results, with aqueous solutions giving rise to various colours, depending upon the size of the particles.

Figure 8:
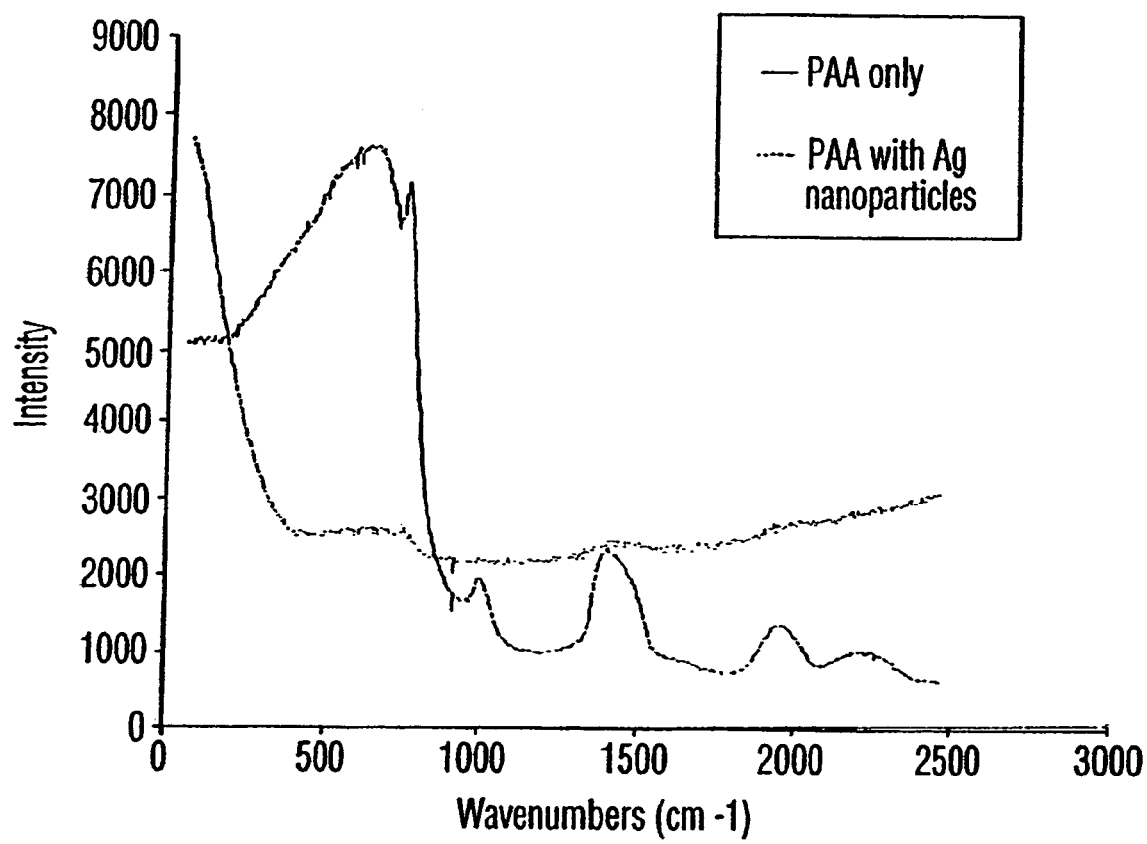
FIG. 8 is Raman spectra of the polyacrylic acid particles and the polacrylic acid silver salt particles of Example 9 below.

Further evidence of encapsulated particles is shown on FIG. 8, Raman spectra, showing the surface enhanced Raman effect of silver nanoparticles on poly acrylic acid, PAA. In the absence of the reduced metal, the Raman peaks for pure polyacrylic acid are hardly discernible, but after the silver salt is reduced to metallic silver, strong enhanced Raman peaks are observable. This is strong evidence for the encapsulation of the silver particles by the remaining polymer from the original particle. This coating can be easily removed by washing with a suitable solvent, or by heating to 300° C. or higher in a reducing atmosphere.

EXAMPLE 10

Larger Particles

Larger particles of polyacrylic acid salts and other polymers for the preparation of metal particles by the process of the invention can be made by emulsion polymerization in the absence of surfactant, by the method of O'Callaghan et.al, *Journal of Applied Plymer Science*, Vol 58, 2047-2055 (1995). This paper describes a method of making monodisperse polymer latices with sizes of 40 nm and higher.

By following the procedure of this paper, there was prepared a copolymer of butyl acrylate (30%) with acrylic acid (70%), cross-linked with 3% divinylbenzene. The average size of these particles was 230±20 nm. Treatment with silver nitrate as in Example 9 followed by laser irradiation with the Nd:YAG laser while stirring the aqueous dispersion gave silver containing nanoparticles about 200 nm in diameter.

What is claimed is:

1. A method of making metal particles, comprising:
   (a) providing internally cross-linked single-polymer molecules;
   (b) contacting the single-polymer molecules with a metal salt to incorporate the metal salt into the single-polymer molecules; and
   (c) causing the metal salt incorporated in the single-polymer molecules to form metal particles.

2. The method of claim 1, wherein step (c) comprises heating the single-polymer molecules having the metal salt incorporated therein.

3. the method of claim 2, wherein the step of heating comprises pyrolysing the polymer.

4. The method of claim 3, wherein residual polymeric material remains after pyrolysis of the polymer.

5. The method of claim 2, wherein the step of heating is conducted in a reducing atmosphere.

6. The method of claim 1, wherein step (c) comprises irradiating the single polymer molecules having the metal salt incorporated therein.

7. The method of claim 6, wherein the irradiation comprises γ-irradiation.

8. The method of claim 1, wherein step (c) comprises reducing the metal salt.

9. The method of claim 1, wherein the metal particles have an average size of less than about 10 nm.

10. The method of claim 9, wherein the metal particles have a size of from about 2.5 nm to about 5 nm.

11. A particle comprising a metal particle and at least a portion of an internally cross-linked single-polymer molecule.

12. The particle of claim 11, wherein the particle is substantially spherical.

13. The particle of claim 12, wherein a layer of the polymer is disposed over the metal particle.

14. The particle of claim 13, wherein the plasmon band intensity of the particle does not change substantially over a period of at least one week.

15. The particle of claim 11, wherein the particle has a size of less than about 10 nm.

16. The particle of claim 15, wherein the particle has a size of about 2.5 nm to about 5 nm.

17. The particle of claim 11, wherein the particle is formed by the process of:
   a) providing internally cross-linked single-polymer molecules;
   b) contacting the single-polymer molecules with a metal salt to incorporate the metal salt into the single-polymer molecules; and
   c) causing the metal salt incorporated in the single-polymer molecules to form metal particles.

* * * * *